United States Patent [19]

Takagi

[11] Patent Number: 5,727,551
[45] Date of Patent: Mar. 17, 1998

[54] NON-CONTACT TONOMETER

[75] Inventor: Akinari Takagi, Tokyo, Japan

[73] Assignee: Topcon Corporation, Tokyo, Japan

[21] Appl. No.: 593,575

[22] Filed: Jan. 30, 1996

[30] Foreign Application Priority Data

Jan. 30, 1995 [JP] Japan .................................. 7-012254

[51] Int. Cl.$^6$ .................................................. A61B 3/16
[52] U.S. Cl. ........................ 128/648; 128/645; 128/646; 128/652
[58] Field of Search .................................. 128/645, 646, 128/647, 648, 649, 650, 651, 652

[56] References Cited

U.S. PATENT DOCUMENTS 4,947,849  8/1990  Takahashi et al. ..................... 128/648

OTHER PUBLICATIONS

Wessels et al., "Tonometer Utilization, Accuracy, and Calibration Under Field Conditions", Arch Ophthalmol, vol. 108, (1990) pp. 1709–1712.

Panek et al., "Intraocular Pressure Measurement with the Tono–Pen Through Soft Contact Lenses", American Journal of Ophthalmology, vol. 109, (1990) pp. 62–65.

Ralston et al., "Glaucoma Screening in Primary Care: The Role of Noncontact Tonometry", The Journal of Family Practice, vol. 34, No. 1, (1992) pp. 73–77.

Britt et al., "Microaerosol Formation in Noncontact 'Air–Puff' Tonometry", Arch Ophthalmol, vol. 109, (1991) pp. 225–228.

Silver et al., "Validity of Pulsatile Ocular Blood Flow Measurements", Survey of Ophthalmology, vol. 38, (1994) pp. 72–80.

*Primary Examiner*—Jennifer Bahr
*Assistant Examiner*—Rosiland Kearney
*Attorney, Agent, or Firm*—Foley & Lardner

[57] ABSTRACT

A non-contact tonometer measures an intraocular pressure precisely based on a deformation amount of a cornea when a pressurized pulse of air is injected to the cornea. The intraocular pressure is measured on the basis of the maximum value of a correlation function curve, instead of detecting a peak of a light changing curve.

20 Claims, 7 Drawing Sheets

FIG.13

NON-CONTACT TONOMETER

BACKGROUND OF THE INVENTION

1. Field of the Invention

The present invention relates to a non-contact tonometer. More particularly, the present invention relates to a non-contact tonometer which measures intraocular pressure based on deformation amount of a cornea when a pressurized pulse of air is injected to the cornea from a nozzle.

2. Background of the Invention

A non-contact tonometer is conventionally known. Such a conventional non-contact tonometer includes an air injector for deforming a cornea by injecting air to a subject eye, a cornea deforming detector for detecting a deformation amount of the cornea based on a change of reflected light received from the cornea that is being projected by a light, a pressure measurer for measuring an air pressure of the air injected by the air injector, with the pressure measurer being located in the air injector. Non-contact tonometers are described in detail in "Tonometer Utilization, Accuracy, and Calibration Under Field Conditions", published in Arch. Ophthalmology, Vol. 108, pages 1709–1712, December 1990; "Intraocular Pressure Measurement With the Tono-Pen Through Soft Contact Lenses", published in American Journal of Ophthalmology 109, pages 62–65, January, 1990; "Glaucoma Screening in Primary Care: The Role of Non-contact Tonometry", published in The Journal of Family Practice, Vol. 34, No.1, pages 73–77 (1992); and "Microaerosol Formation in Noncontact 'Air-Puff' Tonometry", published in Arch. Ophthalmology, Vol. 109, pages 225–228, February 1991. The above-listed articles are incorporated herein by reference.

Figure 9:
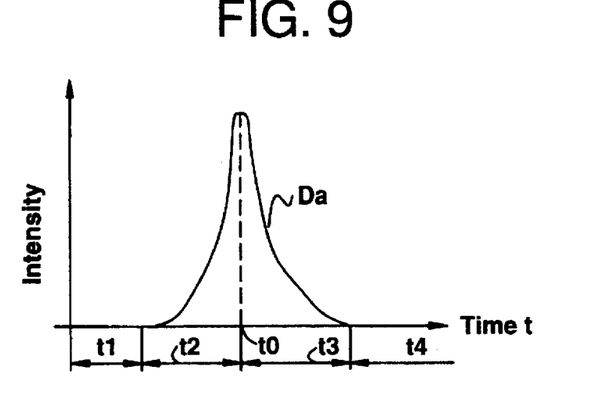
FIG. 9 shows a light changing curve that can be used in the system according to the invention.

In the conventional non-contact tonometer, the air injector injects air to the cornea C from the nozzle by energy obtained from a piston working together with a rotary solenoid. The cornea C is deformed according to a change of air pressure, as shown in FIGS. 8 (a)–(e). FIG. 9 shows an intensity of reflected light that changes depending on the amount of deformation of the cornea C.

FIG. 8 (a) shows a deformation of the cornea C as air starts to be injected to it (corresponding to time period t1 in FIG. 9). FIG. 8 (b) shows a deformation of the cornea C corresponding to the time period t2 in FIG. 9. The cornea C is deformed to a flat, planar surface at the end of time period t2, due to the air pressure being increased after a desired time from start of the air injection to the cornea C.

By increasing the pressure of the injected air, the cornea C is made to a planar surface, or a flat surface, at time t0 in FIG. 9 (corresponding to FIG. 8 (c)). Moreover, by increasing the pressure of the injected air, the cornea C is made concave during time periods t3 and t4 in FIG. 9 (corresponding respectively to FIGS. 8 (d) and 8 (e)).

The intensity of the reflected light from the cornea C increases according to a profile of the cornea C being deformed from a convex shape to a flat shape, as seen in FIG. 9. When the profile of the cornea C becomes flat, the intensity of the reflected light is maximum. The intensity of the reflected light is decreased according to the profile of the cornea C being deformed from the flat shape to a concave shape. The intensity of the reflected light is changed, as shown by the curve Da, from the time t0 to the time t4 in FIG. 9.

Figure 10:
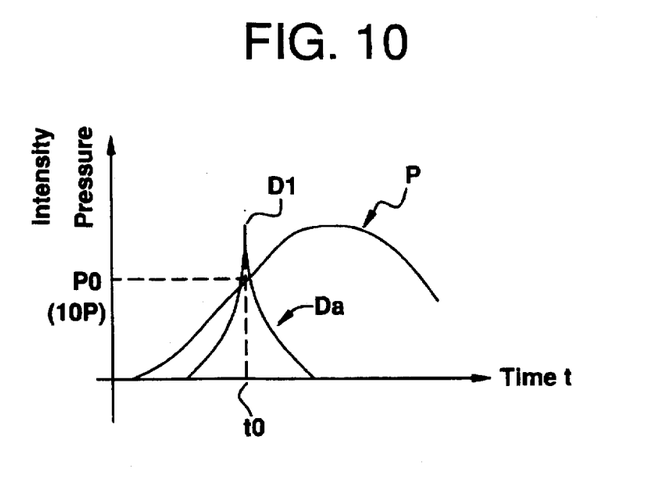
FIG. 10 is a graph showing a relationship between a light changing curve and a pressure changing curve that can be used in the system according to the present invention.

The pressure detected by a pressure detecting sensor over a period of time is shown by a pressure changing curve P in FIG. 10. It is possible to obtain an intraocular pressure Iop based on a value of pressure P0 in the air injector at the time when the curve D1 becomes maximum. This is due to a known relationship between a pressure value in the air injector and an intraocular pressure of the subject eye E.

Figure 11:
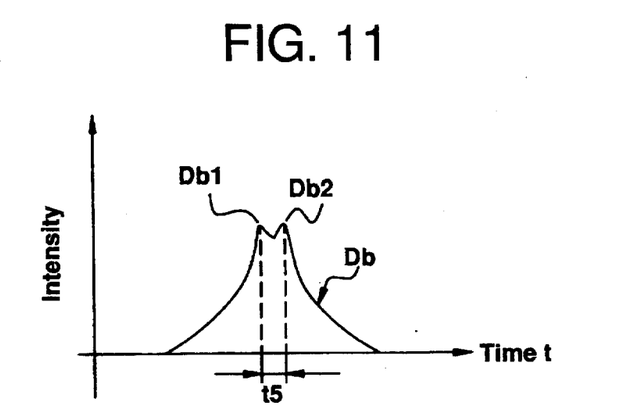
FIG. 11 is a graph showing a light changing curve with two peaks.

However, the peak of the light intensity curve D is not always readily apparent when a profile of the cornea C becomes a flat surface. For example, if some cilia (e.g., eyelashes) are accidentally in an optical path of the cornea deformation detecting optical system before the cornea C attains a flat shape, the intensity of the reflected light is decreased, as shown by the light changing curve Db in FIG. 11, during a time period t5 which includes the time when the cornea C attains a flat shape. In this case, there are two peaks Db1, Db2 at respective times before and after the time when the cornea C becomes flat due to the air pressure applied to it, as shown in FIG. 11.

The intraocular pressure is determined on the basis of either one peak or the other one. It is hard to get accurate intraocular pressure of the subject eye E in this case, because neither the peak Db1 nor the peak Db2 corresponds to the flatness of the cornea C. This results in an uncertainty of an eye measurement, and can lead to a faulty output. A light changing curve of the shape Dc, Dd as shown FIG. 12 and FIG. 13 sometimes occurs due to tearing in the subject eye E, elasticity of a cornea C and/or lack of uniformity of the air being applied to the cornea C.

Figure 12:
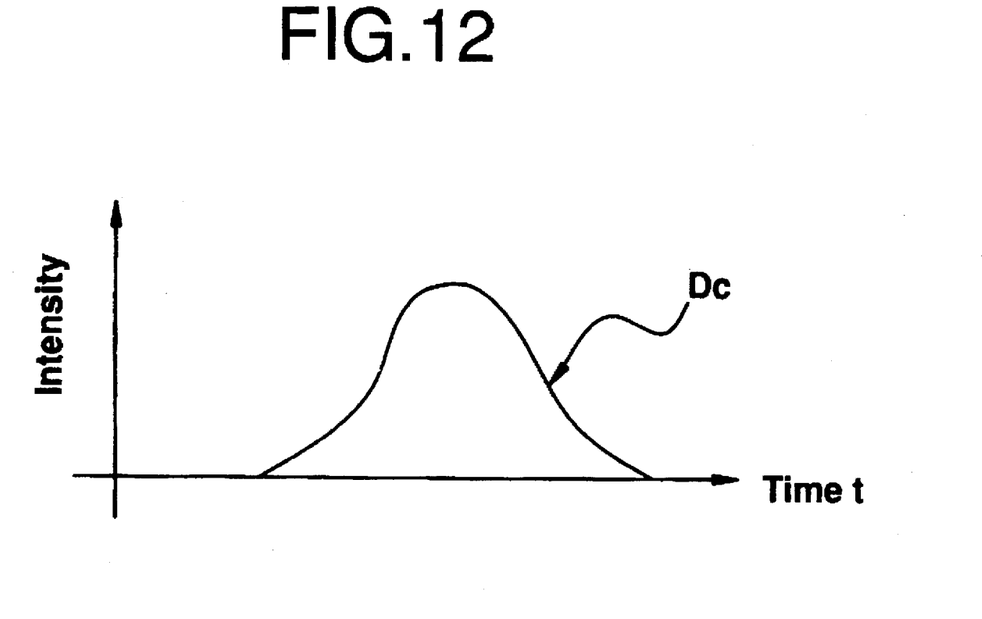
FIG. 12 is a graph showing a light changing curve that has a slightly increasing and a slightly decreasing shape.

A light changing curve of the reflected light as shown FIG. 12 increases gradually. In this case, it is hard to find a peak of the light changing curve and to determine an appropiate measurement timing. As a result, an uncertainty of an eye measurement is likely to occur, and an eye measurement error may occur as a result.

Figure 13:
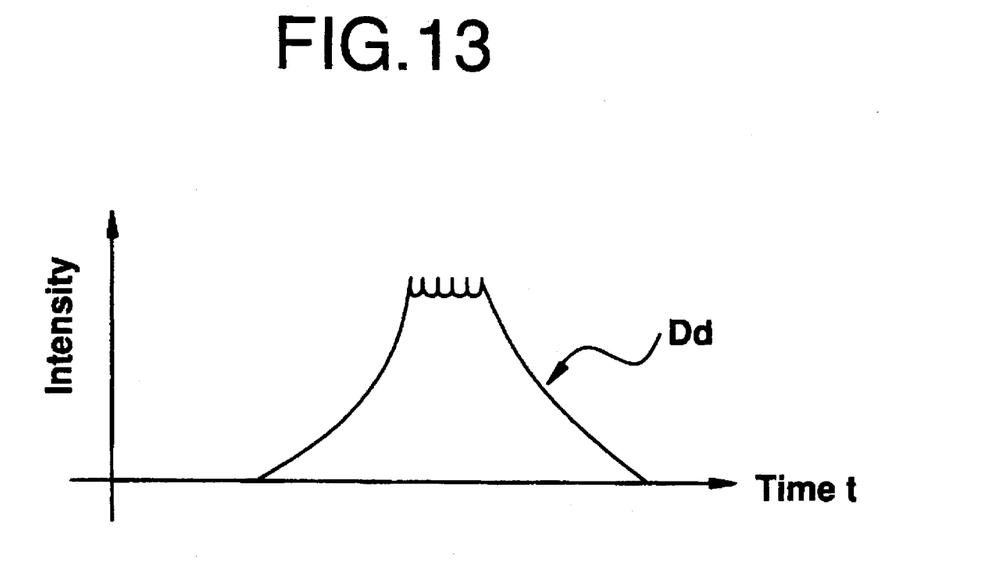
FIG. 13 is a graph showing a light changing curve with several slight peaks.

A light changing curve of the reflected light as shown FIG. 13 includes several slight peaks. In this case as well, it is hard to find a peak of the light changing curve and to determine a measurement timing corresponding to a flat surface condition of the cornea C. Like the other cases described above, an eye measurement error may occur as a result.

SUMMARY OF THE INVENTION

An object of the present invention is to provide an apparatus and a method for measuring accurate intraocular pressure from a signal with various noises in the environment.

A further object of the present invention is to provide an apparatus and a method for measuring accurate intraocular pressure on the basis of a calculated correlation.

A further object of the present invention is to provide an apparatus and a method for measuring accurate intraocular pressure on the basis of a calculated correlation between a standard light value and a light changing value.

A further object of the present invention is to provide an apparatus and a method for measuring accurate intraocular pressure on the basis of a calculated correlation function between a standard light value and a light changing value.

A further object of the present invention is to provide an apparatus and a method for measuring accurate intraocular pressure on the basis of a peak of a calculated correlation function between a standard light value and a light changing value.

BRIEF DESCRIPTION OF THE DRAWINGS

These and other objects and advantages of the invention will become more fully apparent from the following description when read in conjunction with the accompanying drawings, with like reference numerals indicating corresponding parts throughout, wherein:

FIG. 8 (a) shows a cornea C not deformed, having a convex surface;

FIG. 8 (b) shows a cornea C deformed slightly, exhibiting a slightly convex surface;

FIG. 8 (c) shows a cornea C deformed to a flat surface;

FIG. 8 (d) shows a cornea C deformed with a slightly concave surface;

FIG. 8 (e) shows a cornea C deformed with a more concave surface than that shown in FIG. 8 (d);

DESCRIPTION OF THE PREFERRED EMBODIMENTS

A noncontact tonometer of this invention will be described in detail with reference to the accompanying drawings.

Figure 1:
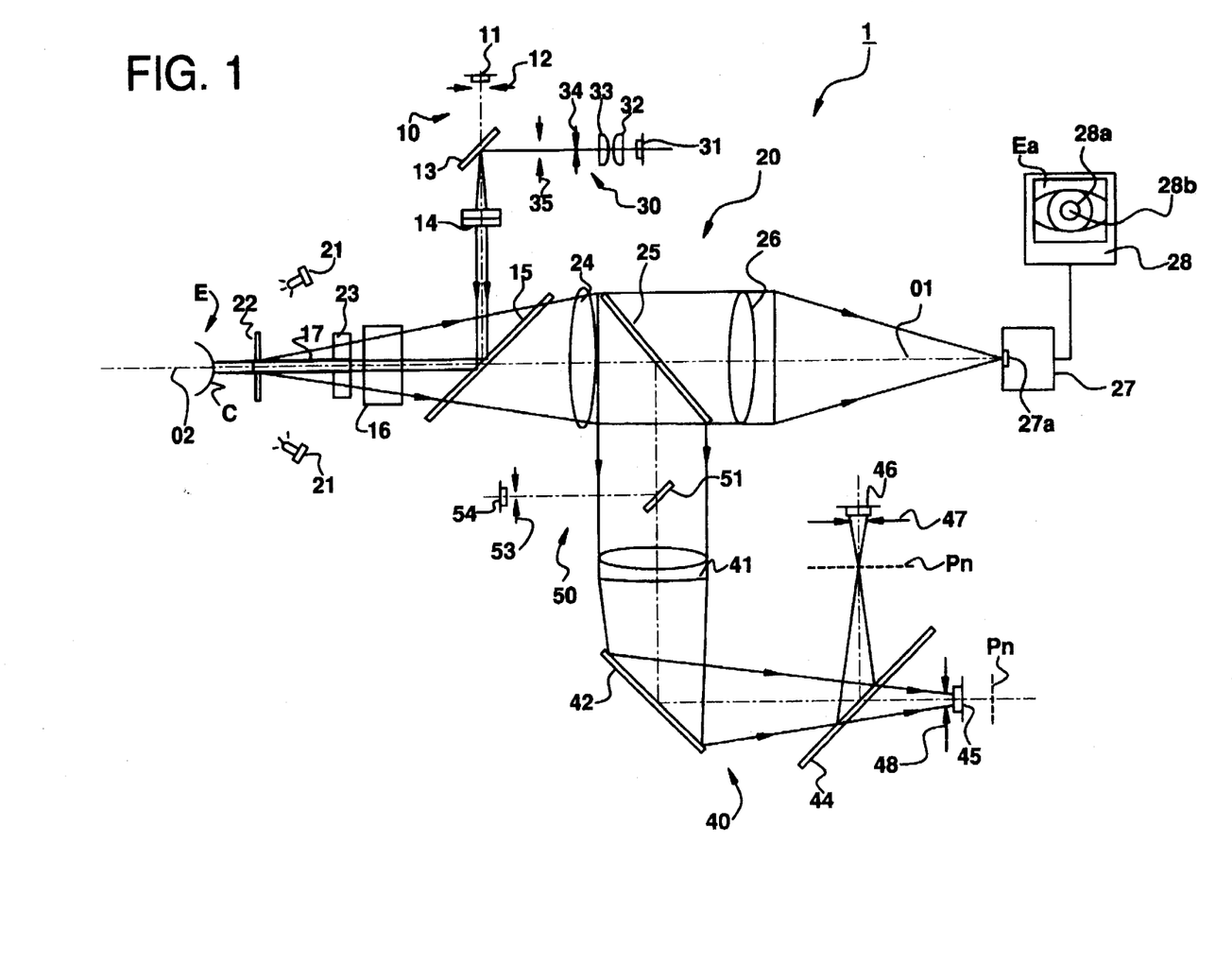
FIG. 1 shows an optical system of a noncontact tonometer of the system according to the present invention, with details showing alignment light and light for observing an anterior part of a subject eye E.
Figure 2:
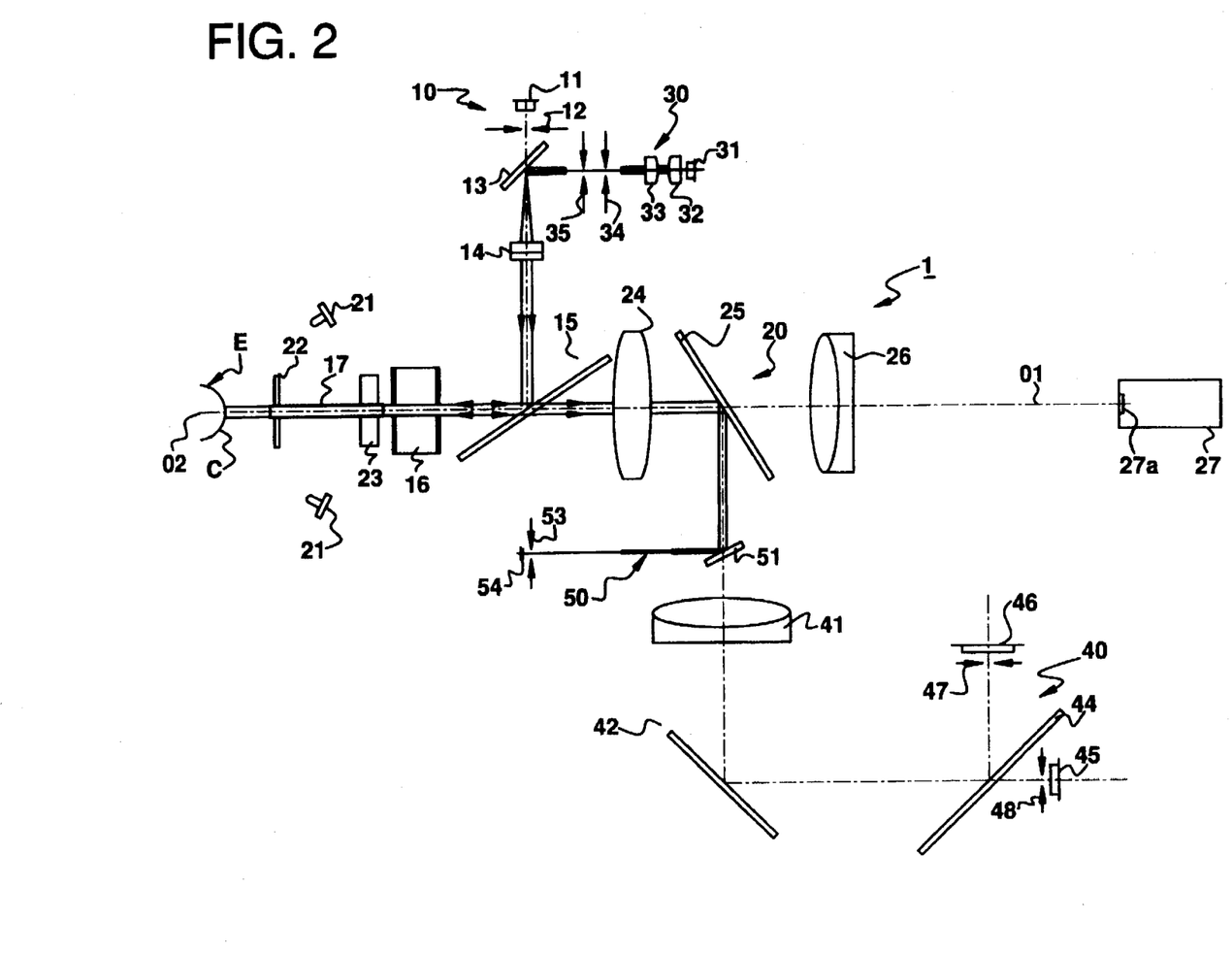
FIG. 2 shows an optical system for detecting a deformation of a subject eye E according to the present invention.

FIG. 1 and FIG. 2 show a non-contact tonometer that includes a fixation target projecting optical system 10 for projecting a fixation target to a subject eye E, an anterior part of the eye observing optical system 20, an alignment light projecting optical system 30 for projecting alignment flux to the subject eye E, an alignment light receiving optical system 40 for detecting an alignment distance away from the subject eye E, and a cornea deformation detecting optical system 50 for detecting the deformation of the cornea C by using an optical factor.

The fixation target projecting optical system 10 includes a light emitted diode (LED) 11, a pinhole 12, a dichroic mirror 13 having characteristics of passing visual light and reflecting near infrared light, a collimator lens 14, a half mirror 15, a chamber window glass 16, and a nozzle 17.

Figure 3:
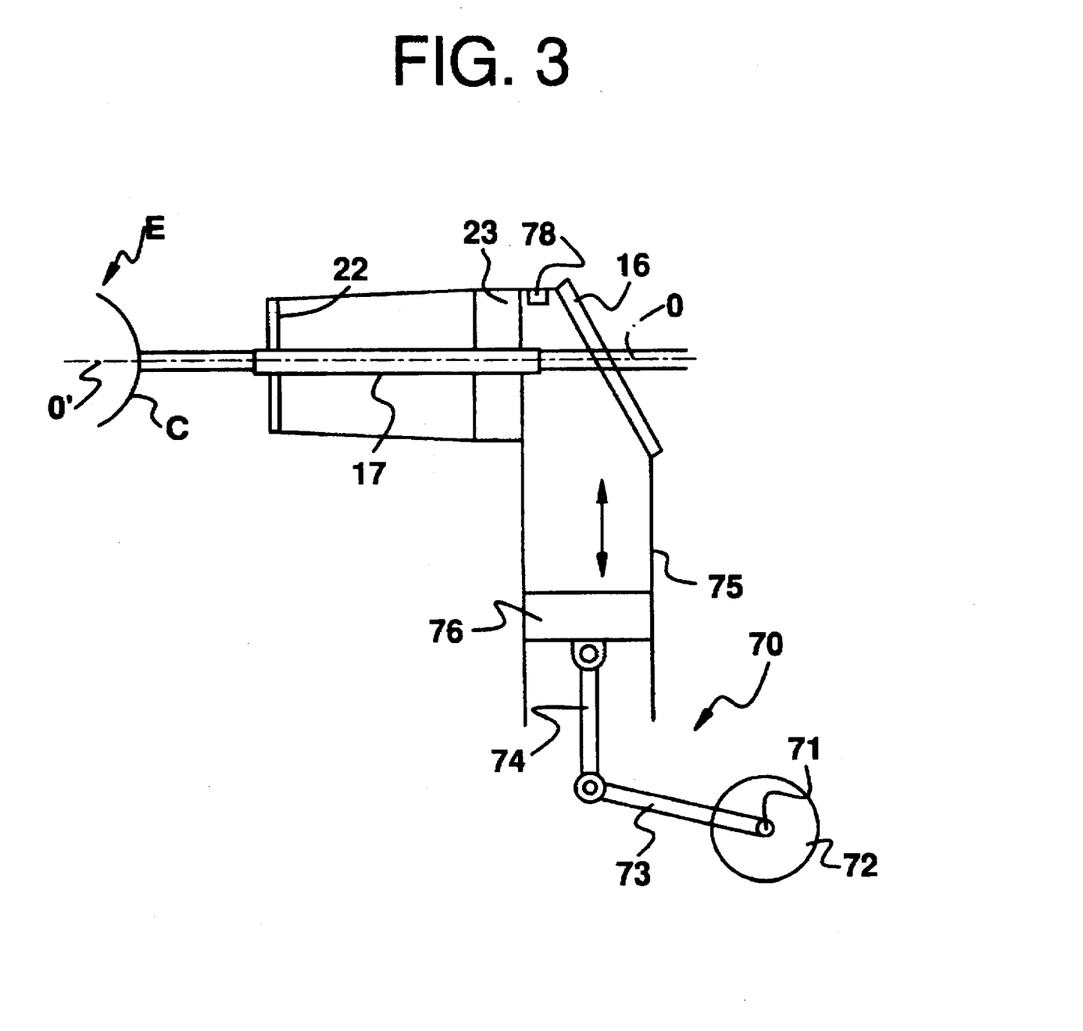
FIG. 3 shows the structure of an air injecting device that can be used in the system according to the present invention.

As seen in FIG. 3, the chamber window glass 16 forms a part of a cylinder 75 of an air injecting device 70 which outputs an air pulse to the nozzle 17. Referring back to FIG. 1, visual light from LED 11 for the fixation target passes through the pinhole 12 and transmits through the dichroic mirror 13, then the transmitted light is collimated by the collimator lens 14 to obtain parallel light.

After the collimated light is reflected by the half mirror 15, the reflected light forms an image in the cornea C of the subject eye E, passing through the chamber window glass 16 and the nozzle 17.

The anterior part of the eye observing optical system 20 comprises plural LEDs 21 which emit infrared light for illuminating the subject eye E directly from a right side and a left side, a cover glass 22 fixed at one end of the nozzle 17, a supporting glass 23 for supporting the other end of the nozzle 17, the chamber window glass 16, the half mirror 15, an objective lens 24, a half mirror 25, an image forming lens 26, and a CCD camera 27.

The infrared light reflected at the subject eye E is collimated by the objective lens 24 in order to form parallel light, after passing through the cover glass 22 and the supporting glass 23. After the collimated light passes through the half mirror 25, the passed light forms an image of the anterior portion of the subject eye E on an imaging device 27a of the CCD camera 27.

In FIG. 1, the anterior portion of the subject eye E is displayed with an alignment area 28a on the imaging device 27a. This alignment area 28a is displayed with an image forming circuit (not shown). The alignment light projecting optical system 30 includes an LED 31 for alignment and for detecting cornea deformation, condenser lenses 32, 33, an aperture 34, a pin hole 35 for forming the image projected to the cornea C, the dichroic mirror 13, the collimator lens 14, the half mirror 15, the chamber window glass 16, and the nozzle 17. The pin hole 35 is conjugated with a back focal point of the condenser lens 14. Infrared light emitted from the LED 31 passes through the condenser lenses 32, 33, the aperture 34 and the pin hole 35, and is then reflected by the dichroic mirror 13.

The reflected light is collimated by the collimator lens 14 to obtain parallel light. After the collimated light is reflected by the half mirror 15, the reflected light is projected to the cornea C of the subject eye E, and the light passes through the chamber window glass 16 and into the nozzle 17.

The projected light is reflected at a surface of the cornea C. The reflected light from the cornea C passes through and is collimated by the cover glass 22, the supporting glass 23 and the half mirror 15. Then, the passed light is collimated by the objective lens 24.

After a part of the collimated light passes through the half mirror 25, that part of the light is formed as a target image 28b by the image forming lens 26. The target image 28b is then displayed on the display 28.

An examiner (i.e., ophthalmologist) moves a main body of the noncontact tonometer either left or right, up or down, or front or back, for placing the target 28b into the alignment area 28a. In case of no alignment of an optical axis 01 of the apparatus with an optical axis 02 of the subject eye E, the target image is moved either up or down, right or left, or in both directions in order to obtain proper alignment.

In case the working distance is too close or too far, the target image is out of focus and unclear, and a size of the target is either too big or too small. Referring to the characteristics of the target image, the examiner can arrange an alignment of the optical axes and a rough working distance of the noncontact tonometer can be obtained.

The alignment light receiving optical system 40 includes an image forming lens 41, a reflecting mirror 42, a half mirror 44, apertures 47, 48, receiving sensors 45, 46, and co-elements from the cover glass 22 through half mirror 25 for the anterior part of the eye observing optical system 20.

The other part of the reflected light from the cornea C is reflected by the half mirror 25 towards the image forming lens 41. The passing light through the image forming lens 41 is reflected by the reflecting mirror 42 towards the half mirror 44. One part of the light from the reflecting mirror 42 passes through the half mirror 44, and the other part of the light is reflected by the half mirror 44. The one part corresponding to the light passing through the half mirror 44 is projected to the receiving sensor 45 through the aperture 48. The other part corresponding to the reflected light that is reflected by the half mirror 44 is projected to the receiving sensor 46 through the aperture 47.

The receiving sensors 45 and 46 are located at a same distance from an image forming position Pn in a front and back direction, respectively. It is possible to have a system such that the receiving sensors 45, 46 and apertures 47, 48 are a same type of device.

The working distance in the Z direction (to the optical axis) is calculated by a calculation device (not shown) on the basis of a ratio of an intensity of the light received by receiving sensor 45 to an intensity of the light received by the receiving sensor 46.

Suppose a level α denotes the intensity of the light received by the receiving sensor 45, and a level β denotes the intensity of the light received by the receiving sensor 46. Then, it is possible to calculate the working distance on the basis of the intensity ratio $\gamma=(\beta-\alpha)/(\beta+\alpha)$.

When the intensity ratio γ is equal to zero (α=β), the appropriate working distance is found. When the intensity ratio γ is greater than zero (γ>0), the working distance is shorter than the appropriate working distance. In other words, the body of the non-contact tonometer is too close to the subject eye E. When the intensity ratio γ is smaller than zero (γ<0), the working distance is longer than the appropriate working distance. In other words, the body of the non-contact tonometer is too far from the subject eye E.

With the system according to the invention, it is possible to detect an alignment condition in an up and down direction, and in a left and right direction (i.e., X direction, Y direction). It is also possible to detect an alignment condition in a Z direction by determining whether both the ratio of the intensities of the receiving sensors 45, 46 are greater than or less than a desired level.

The cornea deformation detecting optical system 50 includes a reflecting mirror 51, an aperture 53, a receiving sensor 54, and co-elements from the cover glass 22 through the half mirror 25 for the anterior part of the eye observing optical system 20.

In FIG. 2, light for detecting projects to the subject eye E at a same time when the air pulse is injected to the subject eye E. This detecting light passes to the cornea C through the condenser lenses 32, 33, the aperture 34, the pin hole 35, the dichroic mirror 13, the collimator lens 14, the half mirror 15, the chamber window glass 16, and the nozzle 17. Then, the detecting light is reflected at the cornea C of the subject eye E. The reflected light from the cornea C is reflected at the half mirror 25, and the reflecting mirror 51 reflects light through the aperture 53 and towards the receiving sensor 54.

Referring now to FIG. 3, the air injecting device 70 includes a cylinder 75, a piston 76 being moved into the cylinder 75 reciprocally, and a rotary solenoid 72 for moving the piston 76 into the cylinder 75 reciprocally. An axis of the rotary solenoid 72 is connected to the piston 76 with a clank arm 73 and a connecting arm 74. The piston 76 is moved into the cylinder 75 reciprocally as driven by the rotary solenoid 72.

Figure 4:
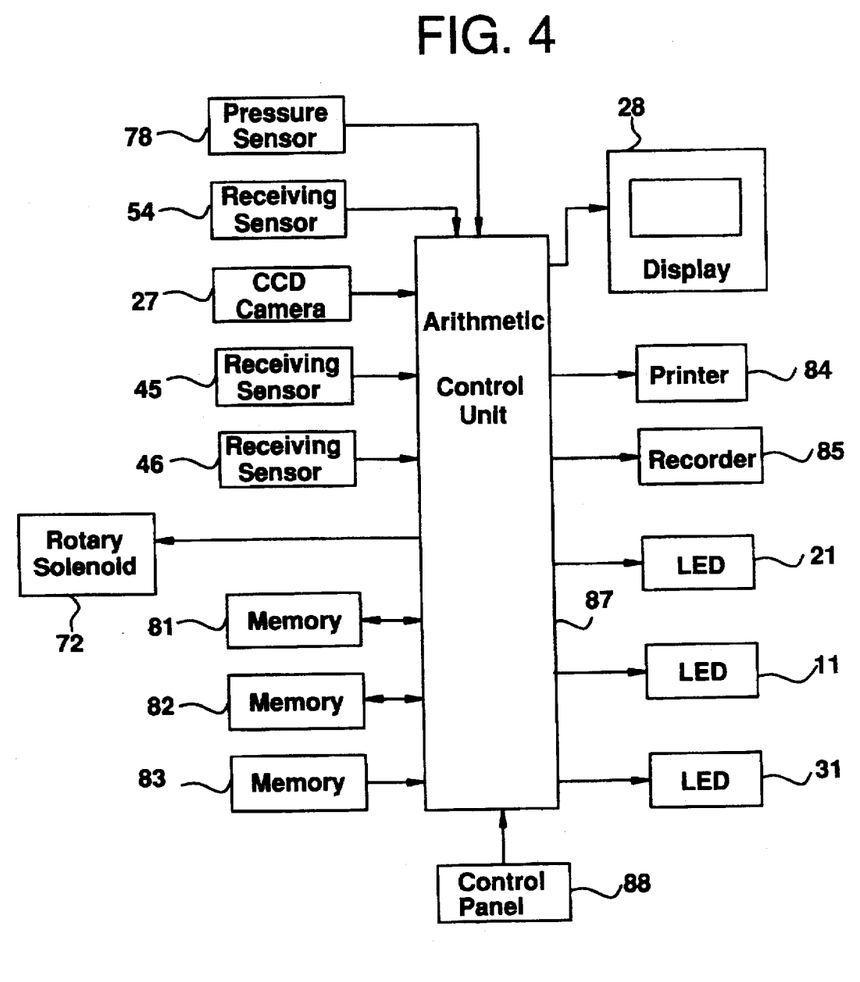
FIG. 4 is a block diagram of a control system of a noncontact tonometer used in the system according to the present invention.

FIG. 4 shows a block diagram of a control system of the non-contact tonometer 1. A pressure detecting sensor 78 for detecting pressure in the cylinder 75 is located at a upper portion of the cylinder 75 in FIG. 3. A memory 81 stores outputs of receiving sensor 54 at periodic instants in time. The memory 81 stores the intensities of the received light signal, such as that given by a light changing curve R shown FIG. 6 (e.g., a light intensity at every 0.1 second).

A memory 82 stores pressure values detected by the pressure detecting sensor 78. In other words, the memory 82 stores the pressure values, such as that given by the pressure changing curve P shown in FIG. 6 (e.g., a pressure value at every 0.1 second).

A memory 83 stores a standard curve F (see FIG. 5) showing an ideal light changing curve of the receiving sensor 54 on the basis of the deformation of the cornea C.

Figure 5:
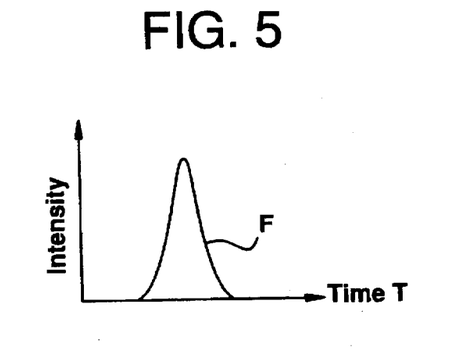
FIG. 5 shows a standard curve used in the system according to the present invention.

One of ordinary skill in the art will recognize that it is possible to choose several different ways to determine the standard curve on the basis of calculated values with simulation or real detected values.

A printer 84 prints out an output of measured intraocular pressure. A recorder 85 records measurement data including the measured intraocular pressure. An arithmetic control unit 87 includes a CPU, which controls the LEDs 11, 21, 31, the printer 84, and the recorder 85 on the basis of orders received from a control panel 88.

The arithmetic control unit 87 obtains the light changing curve R on the basis of the data stored in the memory 83, then it obtains a cross correlation function on the basis of a comparison between the calculated light changing curve R and the standard curve F stored in the memory 83. Moreover, the arithmetic control unit 87 obtains a correlation curve S as shown FIG. 6 on the basis of the cross correlation function.

The cross correlation function is defined by the following equation:

$$r(x') = \frac{\int f(x) * g(x-x')dx}{\sqrt{\int [f(x)]^2 dx * \int [g(x-x')]^2 dx}}$$

wherein f(x) and g(x) are functions of parameter x.

In the system according to the invention, a value of the correlation function S(Δt) is obtained on the basis of n samples of a receiving signal value and a standard value from a value of a standard curve, $(R_{r1}, F_{r1+\Delta t})$, $(R_{r2}, F_{r2+\Delta t})$ ... $(R_{rn}, F_{rn+\Delta t})$.

$$S(\Delta t) = \frac{\Sigma(R_{rk} - \bar{R})(F_{rk+\Delta t} - \bar{F})}{\sqrt{[\Sigma(R_{rk}-\bar{R})]^2[\Sigma(F_{rk+\Delta t}-\bar{F})]^2}}$$

In the above equation, $\bar{F}$ is a mean value of $F_{rk}$, and $\bar{R}$ is a mean value of $R_{rk}$. Then, the correlation function curve S is computed on the basis of S(Δt) by changing the factor Δt gradually. The arithmetic control circuit 87 obtains the intraocular pressure on the basis of a pressure of the pressure changing curve P corresponding to the maximum of the correlation function curve S. The arithmetic control circuit 87 also detects alignment information on the basis of the signals received from the receiving sensors 45, 46.

The operation of the system according to the invention will be explained hereinbelow. After the LEDs 11, 21, 31 turn on, the anterior part of the subject eye and the alignment area 28a are displayed on a display 28. The examiner performs a rough alignment by moving the body of the non-contact tonometer, for moving the target image 28b by LED 31 into the alignment area 28a on the display 28.

In case where the target image 28b enters in the circle mark, the arithmetic control circuit 87 determines that the X-Y directional (up and down, left and right) alignment is correct.

The examiner then performs a Z direction (optical axis) alignment by moving the body of the non-contact tonometer along the Z direction (optical axis). When the non-contact tonometer is located at the appropriate working distance, the arithmetic control circuit 87 determines the appropriate Z direction alignment on the basis of the light levels received by the receiving sensors 45 and 46 being nearly the same (or exactly the same).

After X, Y, Z directional alignments have been done, the examiner operates a measurement start button (not shown). The arithmetic control circuit 87 controls the rotary solenoid 72 when the correct X, Y, Z directional alignment is made. The piston 76 moves upwardly into the cylinder 75 according to this control.

An air pulse is injected from the nozzle 17 to the cornea C in accordance with the movement of the piston 76. The cornea C is deformed toward a concave direction due to the injected air pulse. The anterior part deformed by the air pulse is displayed on the display 28 through the anterior part of the eye observing optical system 20.

Reflected light (parallel flux) based on a cornea deformation is conducted to receiving sensor. The reflected light reaches the receiving sensor 54 after reflecting off of the cornea C into the nozzle 17, through the chamber window 16 and the half mirror 15. The light is then converged by the objective lens 24, reflected at the half mirror 25 and the reflecting mirror 51, and an image is formed on the aperture 53 (shown by the solid lines in FIG. 2). A received light level of the receiving sensor 54 varies in accordance with the amount of deformation of the cornea C. The receiving sensor 54 outputs a signal corresponding to the deformation of the cornea C.

The arithmetic control circuit 87 includes the memory 81 which stores the value of the light received by the receiving sensor 54. The intensity of the reflected light of the receiving sensor 54 is shown as the light changing curve R (see FIG. 6) in accordance with the amount of deformation of the cornea C caused by the injected air pulse.

Figure 6:
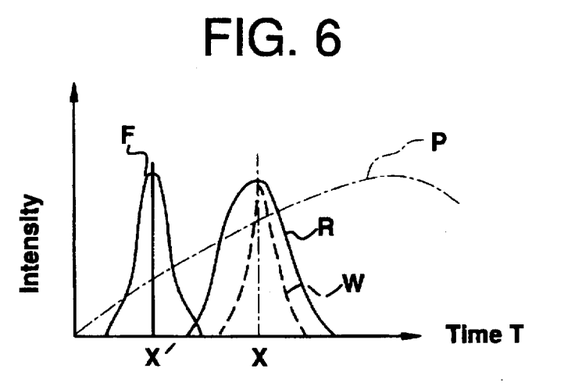
FIG. 6 is a graph showing a relationship between a standard curve and a light changing curve that is used in the system according to the present invention.
Figure 7:
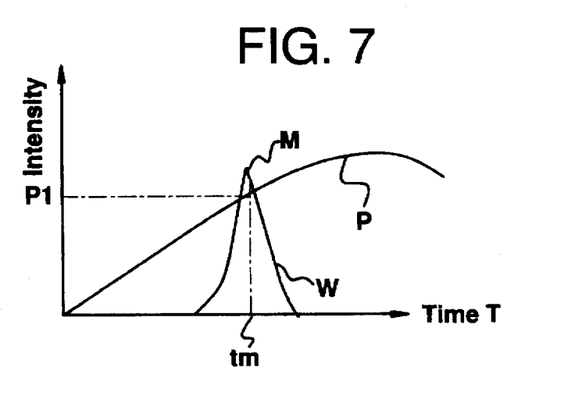
FIG. 7 is a graph showing a relationship between a correlation curve and a pressure changing curve that is used in the system according to the present invention.
Figure 8A:
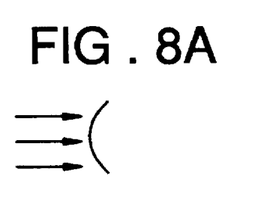
Figure 8B:
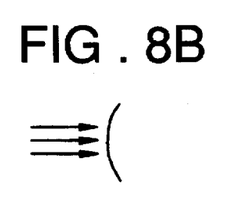
Figure 8C:
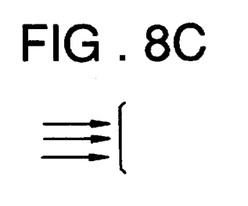
Figure 8D:
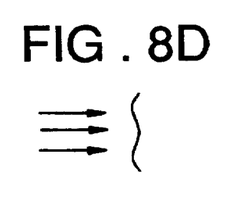
Figure 8E:
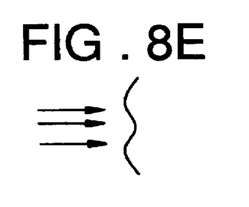

The memory 81 stores a receiving signal value indicative of the light changing curve R. The pressure sensor 78 detects the air pressure in the cylinder 75, in other words, the pressure of the air pulse injected from the nozzle 17. A pressure in the cylinder 75, as shown by the pressure changing curve P in FIG. 6, is changed in accordance with a movement of the piston 76. The memory 82 stores a pressure signal value indicative of the pressure changing curve P.

After injecting of the air pulse, the arithmetic control circuit 87 obtains the value $S(\Delta t)$, on the basis of the standard curve F stored in the memory 81 and the light changing curve R. Then, the arithmetic control circuit 87 obtains the correlation function curve W as shown FIG. 6 on the basis of the value $S(\Delta t)$, and obtains the maximum value M of the correlation function curve W.

It is possible to obtain the maximum M of the correlation function curve W after performing a spline interpolation to the correlation function curve W.

It is also possible to obtain the maximum M of the correlation function curve W after approximating the correlation function curve W as a Gaussian curve by a least-squares estimation method.

The arithmetic control circuit 87 obtains a time tm corresponding to the maximum value M, and obtains a pressure P1 at the time tm on the basis of the pressure changing curve P corresponding to the data stored in the memory 82. Then, the arithmetic control circuit 87 obtains an intraocular pressure of the subject eye E on the basis of the pressure P1 at time tm.

In case of elasticity of the subject eye E, non-uniformity of the air, tearing in the subject eye E, blockage caused by cilia of the subject eye E, an alignment miss etc., a real peak sometimes does not appear in the output signal of the light receiving sensor. In this case, it is possible to find the real peak of the detected signal on the basis of the maximum value M of the correlation function curve W according to the present invention.

In that case, it is possible to make sure of the reliability of measurement on the basis of the maximum value M of the correlation function curve W according to the present invention.

In the present invention, it is possible to measure the intraocular pressure accurately, because the intraocular pressure is measured on the basis of the maximum value M of the correlation function curve S, instead of detecting a peak of the light changing curve R.

As a result, it is possible to avoid unwanted (e.g., noisy) influences due to elasticity of the cornea C, non-uniformity of the air, tearing in the subject eye E, blockage caused by cilia of the subject eye E, an alignment miss, etc.

In cases where it is hard to detect the real peak from the detected signal using conventional non-contact tonometers, it is possible to find the real peak of the signal which corresponds to the cornea C having a planar (flat surface) in accordance with the present invention. Then, it is possible to obtain a precise intraocular pressure, and a measurement result with high accuracy.

In the system described above, the pressure value detected by the pressure sensor 78 is used for obtaining the intraocular pressure. However, it is also possible to use the time corresponding to the peak of the correlation function curve W to obtain the intraocular pressure, in a condition with the air injecting device of which the air-injecting time is predetermined.

It is also possible to select a standard curve from a plurality of standard curves in accordance with a measurement condition, etc. For example, two standard curves for high pressure and low pressure, respectively, can be utilized in the system according to the invention. With this example, in a case where the intraocular pressure is higher than 30 mmHg, the standard curve corresponding to the high pressure is selected for measuring. In a case where the intraocular pressure is less than 30 mmHg, the standard curve corresponding to the low pressure is selected for measuring.

While a preferred embodiment of the invention has been described herein, modification of the described embodiment may become apparent to those of ordinary skill in the art, following the teachings of the invention, without departing from the scope of the invention as set forth in the appended claims.

What is claimed is:

1. An apparatus for measuring an intraocular pressure of a subject eye, comprising:

an injecting device configured to deform a cornea of said subject eye by injecting a substance at said cornea over a first predetermined time period in a range from a first injecting pressure to a second injecting pressure;

a projecting device configured to project light at said cornea;

a light receiving device configured to receive reflected light from said cornea and to output a light signal as a result thereof;

a memory configured to store a reference curve, said reference curve corresponding to ideal received light intensities obtainable within a second predetermined time period;

a correlation calculating device connected to said light receiving device and said memory, said correlation calculating device configured to calculate a correlation between said reference curve and a light changing curve which corresponds to a curve based on the light signal output by said light receiving device within the first predetermined time period; and an intraocular pressure measuring device connected to said correlation calculating device and configured to measure said intraocular pressure of said subject eye on a basis of said correlation.

2. The apparatus according to claim 1, wherein said correlation calculating device calculates a correlation function as said correlation, and wherein said intraocular pressure measuring device measures said intraocular pressure of said subject eye on a basis of said correlation function.

3. The apparatus according to claim 2, wherein said intraocular pressure measuring device measures said intraocular pressure of said subject eye on a basis of a peak of said correlation function.

4. The apparatus according to claim 1, wherein said reference curve is based on one of simulations and a composite of previously obtained light intensity curves over particular time periods.

5. An apparatus for measuring an intraocular pressure of a subject eye, comprising:

a injecting device configured to deform a cornea of said subject eye by injecting a substance at said cornea over a first predetermined time period in a range from a first injecting pressure to a second injecting pressure;

a projecting device configured to project light at said cornea;

a light receiving device configured to receive reflected light from said cornea and to output a light signal as a result thereof;

a pressure detecting device connected to said injecting device and configured to detect a pressure of said substance injected by said injecting device;

a memory configured to store a reference curve, said reference curve corresponding to ideal received light intensities obtainable within a second predetermined time period;

a correlation calculating device connected to said memory and said light receiving device, said correlation calculating device configured to obtain a correlation between said reference curve and a light changing curve which corresponds to a curve based on the light signal output by said light receiving device within the first predetermined time period; and an intraocular pressure measuring device connected to said correlation calculating device and configured to measure said intraocular pressure of said subject eye on a basis of said correlation and said pressure detected by said pressure detecting device.

6. The apparatus according to claim 5, wherein said correlation calculating device calculates a correlation function as said correlation, and wherein said intraocular pressure measuring device measures said intraocular pressure of said subject eye on a basis of said correlation function and said pressure detected by said pressure detecting device.

7. The apparatus according to claim 6, wherein said intraocular pressure measuring device measures said intraocular pressure of said subject eye on a basis of a peak of said correlation function and said pressure detected by said pressure detecting device.

8. An apparatus for measuring an intraocular pressure of a subject eye, comprising:

injecting means for deforming a cornea of said subject eye by injecting a substance at said cornea over a first predetermined time period in a range from a first injecting pressure to a second injecting pressure;

projecting means for projecting light at said cornea;

light receiving means for receiving reflected light from said cornea and for outputting a light signal as a result thereof;

a memory for storing a reference curve, said reference curve corresponding to ideal received light intensities obtainable over a second predetermined time period;

correlation calculating means for obtaining a correlation between said reference curve and a light changing curve which corresponds to a curve based on the light signal output by said light receiving means within the first predetermined time period; and intraocular pressure measuring means for measuring said intraocular pressure of said subject eye on a basis of said correlation.

9. The apparatus according to claim 8, wherein said correlation calculating means calculates a correlation function as said correlation, and wherein said intraocular pressure measuring means measures said intraocular pressure of said subject eye on a basis of said correlation function.

10. The apparatus according to claim 9, wherein said intraocular pressure measuring means measures said intraocular pressure of said subject eye on a basis of a peak of said correlation function.

11. An apparatus for measuring an intraocular pressure of a subject eye, comprising:

injecting means for deforming a cornea of said subject eye by injecting a substance at said cornea over a first predetermined time period in a range from a first injecting pressure to a second injecting pressure;

projecting means for projecting light at said cornea;

light receiving means for receiving reflected light from said cornea and for outputting a light signal as a result thereof;

pressure detecting means for detecting a pressure of said substance injected by said injecting means;

a memory for storing a reference curve, said reference curve corresponding to ideal received light intensities obtainable over a second predetermined time period;

correlation calculating means for obtaining a correlation between said reference curve and a light changing curve which corresponds to a curve based on the light signal output by said light receiving means within the first predetermined time period; and intraocular pressure measuring means for measuring said intraocular pressure of said subject eye on a basis of said correlation and said pressure detected by said pressure detecting means.

12. The apparatus according to claim 11, wherein said correlation calculating means calculates a correlation function as said correlation, and wherein said intraocular pressure measuring means measures said intraocular pressure of said subject eye on a basis of said correlation function and said pressure detected by said pressure detecting means.

13. The apparatus according to claim 12, wherein said intraocular pressure measuring means measures said intraocular pressure of said subject eye on a basis of a peak of said correlation function and said pressure detected by said pressure detecting means.

14. A method for measuring an intraocular pressure of a subject eye, comprising the steps of:

injecting a substance at a cornea of said subject eye for deforming said cornea, the injecting being performed over a first time period in a range from a first injecting pressure to a second injecting pressure;

projecting light at said cornea;

receiving reflected light from said cornea;

calculating a correlation between a reference curve and a light changing curve which corresponds to the received reflected light, said reference curve corresponding to ideal received light intensities obtainable over a second time period; and measuring said intraocular pressure of said subject eye on a basis of said calculated correlation.

15. The method according to claim 13, wherein said correlation calculating step calculates a correlation function as said correlation, and wherein said measuring step measures said intraocular pressure of said subject eye on a basis of said correlation function.

16. The method according to claim 15, wherein said measuring step measures said intraocular pressure of said subject eye on a basis of a peak of said correlation function.

17. A method for measuring an intraocular pressure of a subject eye, comprising the steps of:

injecting a substance at a cornea of said subject eye for deforming said cornea, the injecting being performed over a first time period in a range from a first injecting pressure to a second injecting pressure;

projecting light at said cornea;

receiving a reflected light from said cornea;

detecting a pressure of said injected substance;

calculating a correlation between a reference curve and a light changing curve which is based on the received reflected light, said reference curve corresponding to ideal received light intensities obtainable over a second time period; and measuring said intraocular pressure of said subject eye on a basis of said calculated correlation and said detected pressure.

18. The method according to claim 17, wherein said correlation calculating step calculates a correlation function as said correlation, and wherein said measuring step measures said intraocular pressure of said subject eye on a basis of said correlation function and said detected pressure.

19. The method according to claim 18, wherein said measuring step measures said intraocular pressure of said subject eye on a basis of a peak of said correlation function and said detected pressure.

20. The method according to claim 16, wherein said reference curve is based on one of simulations and a composite of previously obtained light intensity curves over particular time periods.

* * * * *